United States Patent [19]

Goto et al.

[11] Patent Number: 4,772,416
[45] Date of Patent: Sep. 20, 1988

[54] PHENYLPYRIDINE DERIVATIVE

[75] Inventors: Yasuyuki Goto; Kazunori Nigorikawa; Toyoshiro Isoyama, all of Kanagawa, Japan

[73] Assignee: Chisso Corporation, Osaka, Japan

[21] Appl. No.: 28,690

[22] Filed: Mar. 20, 1987

[30] Foreign Application Priority Data

Apr. 1, 1986 [JP] Japan .................... 61-75120

[51] Int. Cl.$^4$ .......... G02F 1/13; C09K 19/34; C07D 211/72; C07D 211/84
[52] U.S. Cl. .......... 252/299.61; 252/299.5; 350/350 R; 350/350 S; 546/330; 546/339; 546/346; 546/348
[58] Field of Search .......... 252/299.5, 299.61, 299.63; 350/350 R, 350 S; 546/330, 339, 346, 348

[56] References Cited

U.S. PATENT DOCUMENTS

| | | | |
|---|---|---|---|
| 4,545,922 | 10/1985 | Eidenschink et al. | 252/299.63 |
| 4,620,938 | 11/1986 | Römer et al. | 252/299.63 |
| 4,640,795 | 2/1987 | Ogawa et al. | 252/299.61 |
| 4,659,500 | 4/1987 | Sugimori et al. | 252/299.61 |
| 4,684,220 | 8/1987 | Shionozaki et al. | 252/299.61 |
| 4,684,477 | 8/1987 | Sugimori et al. | 252/299.61 |
| 4,695,398 | 9/1987 | Goto et al. | 252/299.63 |
| 4,713,197 | 12/1987 | Eidenschink et al. | 252/299.61 |

FOREIGN PATENT DOCUMENTS

| | | | |
|---|---|---|---|
| 194153 | 9/1986 | European Pat. Off. | 252/299.61 |
| 3315295 | 10/1984 | Fed. Rep. of Germany | 252/299.61 |
| 3515373 | 11/1986 | Fed. Rep. of Germany | 252/299.61 |
| 86/06401 | 11/1986 | PCT Intl Appl. | 252/299.61 |
| 2092169 | 8/1982 | United Kingdom | 252/299.61 |
| 2153345 | 8/1985 | United Kingdom | 252/299.61 |
| 2161808 | 1/1986 | United Kingdom | 252/299.61 |
| 1069413 | 4/1985 | U.S.S.R. | 252/299.61 |
| 1063100 | 6/1985 | U.S.S.R. | 252/299.61 |
| 1063101 | 6/1985 | U.S.S.R. | 252/299.61 |

OTHER PUBLICATIONS

Demus, D., et al., Flüssige Kristalle in Tabellen, VEB Deutscher Verlag for Grundstoffinbustrie, Leipzig, pp. 254-255 (1974).
Karamysheva, L. A., et al., Mol. Cryst. Liquid Crystl., vol. 67, pp. 241-252 (1981).
Pavluchenko, A. I., et al., Abstract I30, Abstracts of the Tenth International Liquid Crystal Conference, York, U.K. (Jul. 15-21, 1984).
Pavluchenko, A. I., et al., Advances in Liquid Crystal Research and Applications, Data L., Pergamon Press, Oxford, pp. 1007-1013 (1980).
C.A., vol. 102, 149052 (17).
Grebyonkin, M. F., et al., Mol. Cryst. Liq. Cryst., vol. 129, pp. 245-257 (1985).

Primary Examiner—Teddy S. Gron
Attorney, Agent, or Firm—Wenderoth, Lind & Ponack

[57] ABSTRACT

A novel phenylpyridine derivative which exhibits a positive dielectric anisotropy and is useful as a component of liquid crystal materials and also has a broad temperature range of liquid crystal phases, a high clearing point and a superior compatibility with other liquid crystal compounds or liquid crystal compositions, and a composition containing the derivative are provided. The phenylpyridine derivative is expressed by the formula

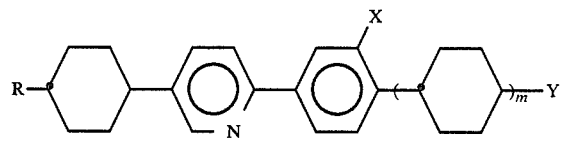

wherein R represents an alkyl group of 1 to 10 carbon atoms, X represents H or F; Y represents F, —CN or an alkyl group or an alkoxy group of 1 to 10 carbon atoms; and m represents 0 or 1.

4 Claims, No Drawings

PHENYLPYRIDINE DERIVATIVE

BACKGROUND OF THE INVENTION
1. Field of the Invention

This invention relates to a novel compound having a positive dielectric anisotropy which is useful as a component of liquid crystal materials, and a liquid crystal composition containing the same.

2. Description of the Related Art

The display mode of liquid crystal display elements utilizing optical anisotropy and dielectric anisotropy includes various modes such as twisted nematic (TN) type, dynamic scattering (DS) type, guest-host type, DAP type, etc., and the properties desired for liquid crystal compositions used vary depending on the respective modes. It has been required for any of the liquid crystal substances to be stable to moisture, air, heat, light, etc. and those exhibiting liquid crystal phases within as broad a temperature range as possible, around room temperature. At present, however, there is no single compound which satisfies such conditions so that several kinds of liquid crystal compounds have been mixed together and if necessary, non-liquid crystal compounds have been further mixed, for practical use.

Namely, it has generally been required for liquid crystal compositions used for display elements that in addition to the presence of liquid crystal phases within a broad temperature range including service temperatures, the viscosity is low; the operating threshold voltage is sufficiently small to be able to effect driving with a small power; the operating response rate is high; etc.

Some compounds which are similar in the structure to the compounds of the present invention are disclosed in some literature mentioned below.

Japanese patent application laid-open No. Sho 61-204168/1986 discloses a liquid crystal compound expressed by the formula

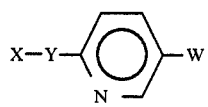 (1)

wherein X represents F or Cl, Y represents

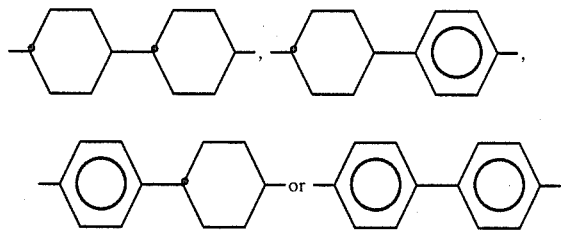

and W represents cyano or an alkyl group of 2 to 15 carbon atoms.

Japanese patent application laid-open No. Sho 61-163864/1986 discloses a liquid crystal compound expressed by the formula

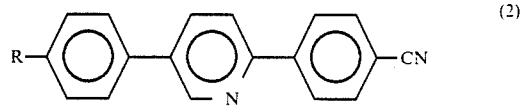 (2)

wherein R represents an alkyl group or an alkoxy group of 4 to 8 carbon atoms.

Japanese patent application laid-open No. Sho 61-246167/1986 discloses a liquid crystal compound expressed by the formula

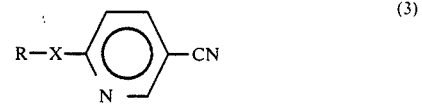 (3)

wherein R represents an alkyl group or an alkoxy group of 1 to 10 carbon atoms and X represents

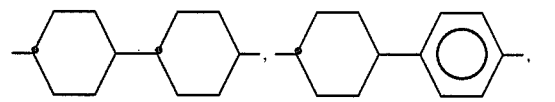

Further, D. Demus et al, "Flüssige Kristalle in Tabellen" (1974), pp 254 (issued by VEB Deutscher Verlag für Grundstoffindustrie ) discloses a liquid crystal compound expressed by the formula

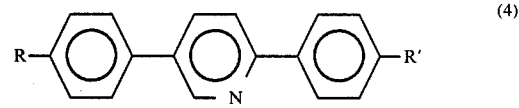 (4)

wherein R and R' each represent an alkyl group of 1 to 6 carbon atoms.

SUMMARY OF THE INVENTION

The object of the present invention is to provide a novel compound which, when added to liquid crystal substances, can improve some of the characteristics required for the resulting liquid crystal compositions.

The present invention in a first aspect resides in (1) a phenylpyridine derivative expressed by the formula

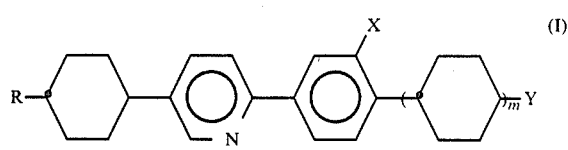 (I)

wherein R represents an alkyl group of 1 to 10 carbon atoms; X represents H or F; Y represents F, —CN or an alkyl group or an alkoxy group of 1 to 10 carbon atoms; and m represents 0 or 1, and its embodiments are shown in the following items (2)–(5):

(2) 5-(Trans-4-alkylcyclohexyl)-2-(4-substituted phenyl)pyridines according to item (1) wherein, in the formula (I), R represents an alkyl group of 1 to 10 carbon atoms; X represents H; Y represents F or —CN; and m represents 0.

(3) 5-(Trans-4-alkylcyclohexyl)-2-(3-fluoro-4-substituted phenyl)pyridines according to item (1) wherein, in the formula (I), R represents an alkyl group of 1 to 10 carbon atoms; X represents F; Y represents F or —CN; and m represents 0.

(4) 5-(Trans-4-alkylcyclohexyl)-2-(4-substituted phenyl)pyridines according to item (1) wherein in the formula (I), R represents an alkyl group of 1 to 10 carbon atoms; X represents H; Y represents an alkyl group or an alkoxy group of 1 to 10 carbon atoms; and m represents 0.

(5) 5-(Trans-4-alkylcyclohexyl)-2-[4-(trans-4-alkylcyclohexyl)phenyl]pyridines according to item (1) wherein in the formula (I), R represents an alkyl group of 1 to 10 carbon atoms; X represents H; Y represents an alkyl group of 1 to 10 carbon atoms; and m represents 1.

The present invention in a second aspect resides in (6) a liquid crystal composition containing at least two components, wherein at least one component is a phenylpyridine according to item (1) and consisting of at least two components.

DETAILED DESCRIPTION OF PREFERRED EMBODIMENTS

Examples of the compounds of the present invention are
5-(trans-4-alkylcyclohexyl)-2-(4-fluorophenyl)pyridines,
5-(trans-4-alkylcyclohexyl)-2-(3,4-difluorophenyl)pyridines,
5-(trans-4-alkylcyclohexyl)-2-(4-cyanophenyl)pyridines,
5-(trans-4-alkylcyclohexyl)-2-(3-fluoro-4-cyanophenyl)pyridines,
5-(trans-4-alkylcyclohexyl)-2-(4-alkylphenyl)pyridines,
5-(trans-4-alkylcyclohexyl)-2-(4-alkyloxyphenyl)pyridines, and
5-(trans-4-alkylcyclohexyl)-2-[4-(trans-4-alkylcyclohexyl)phenyl]pyridines, and among these, compounds having a linear chain alkyl group of 1 to 10 carbon atoms as the alkyl moiety are preferred.

The compounds provided by the present invention have a broad liquid crystal phase temperature range and also a high clearing point, and further a superior compatibility with other liquid crystal compounds or liquid crystal mixtures.

Further, the compounds consisting of three rings shown in the above items (2) and (3) have a particularly large dielectric anisotropy value and hence are useful for lowering the threshold voltage of liquid crystal display elements using liquid crystal mixtures having the compounds as a component thereof.

Further, the compounds of the present invention having three six-membered rings without a cyano group have a low viscosity for three-ring-structured compounds and hence they are preferred as a liquid crystal component. For example, compounds of the item (2) wherein Y represents F have a viscosity of ca. 19 cp as measured by extrapolation from a mixture thereof with liquid-crystalline transcyclohexanes at 20° C., and hence the viscosity thereof is very small for compounds having three rings.

Compounds of the item (4) and compounds of the item (5) are both high temperature liquid crystals having a very broad liquid crystal phase temperature range, that is, the ranges of the former compounds are from the vicinity of room temperature to about 170° C. and those of the latter are generally from 90° C. to 300° C. or higher.

As described above, when the compounds of the present invention are blended with other liquid crystal compositions, making use of the specific features of the compounds, it is possible to broaden the liquid crystal phase range thereof, lower the viscosity or lower the driving voltage of liquid crystal display elements almost without raising the viscosity.

The specific features of the compounds of the present invention are shown in Tables 1 and 2, in a comparison of the physical properties thereof with those of compounds having similar chemical structures.

TABLE 1

| Compound | Phase transition point (°C.) | | $\Delta\epsilon$ | $\Delta n$ | $\eta_{20}$ (cp) |
| --- | --- | --- | --- | --- | --- |
| | M.P. | Clearing point | | | |
| $C_3H_7$—⬡—⬡(N)—⬡—F | 99.0 | 157.3 | 15.9 | 0.172 | 19.4 |
| $C_5H_{11}$—⬡—⬡(N)—⬡—F | 95.5 | 154.8 | 12.5 | 0.139 | 36.1 |

TABLE 2

| Compound | Phase transition point (°C.) | |
| --- | --- | --- |
| | M.P. | Clearing point |
| (a) $C_4H_9$—⬡—⬡(N)—⬡—$C_2H_5$ | 35.4 | 173.2 |

TABLE 2-continued

| | Phase transition point (°C.) | |
|---|---|---|
| | M.P. | Clearing point |
| (b) 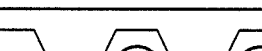 | 89.3 | 175.0 |
| (c)  | 35.0 | 161.8 |

The dielectric anisotropy values (Δε), the optical anisotropy values (Δn) and the viscosity values at 20° C. ($\eta_{20}$) in Table 1 are those sought by extraporation from the values of the physical properties of liquid crystal compositions obtained by adding the above-mentioned respective compounds, each in 15 parts by weight, to 85 parts by weight of the liquid crystal composition (A) in Example 6 mentioned later. The results in Table 1 indicate that in the core structure consisting of three six-membered rings, when the central phenylene ring is replaced by a pyridine ring, the viscosity is reduced and also the Δε and Δn values are increased while the liquid crystal phase temperature range is kept close to that of the liquid crystal mixture containing the compound having the central phenylene ring.

The fact described above relative to the liquid crystal phase temperature range is also confirmed by the results in Table 2. Namely, in the compounds having a core structure consisting of three six-membered rings, replacement of the central phenylene ring by a pyridine ring broadens the range of intermediate phases.

Next, preparation of the compounds of the present invention will be described.

First, a trans-4-alkyl-(β-piperidinovinyl)cyclohexane (II) is reacted with a substituted phenyl β-chlorovinyl ketone (III) in the presence of an amine, followed by heating the resulting material with perchloric acid to obtain a pyrylium salt (IV), thereafter reacting this compound (IV) with ammonium acetate to obtain the objective compound. Another objective cyano compound is prepared by cyanogenating the corresponding bromo compound as obtained above.

The foregoing is illustrated by the following reaction equations:

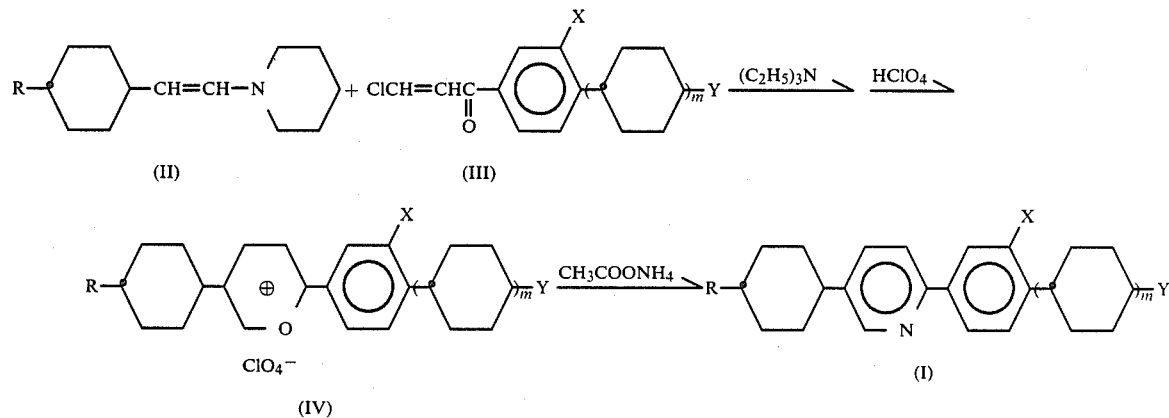

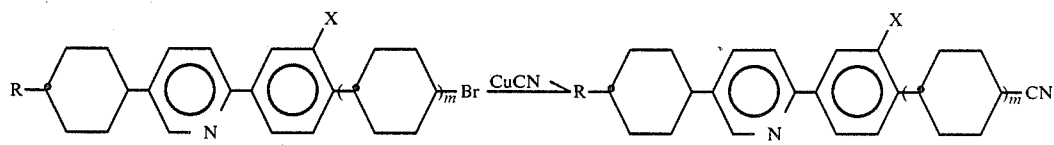

(In these equations, R, X and m are as defined above.)

Concrete examples of compounds other than the phenylpyridine derivatives expressed by the formula (I) and usable as a component of the liquid crystal compositions of the present inventions are ester liquid crystal compounds such as trans-4-alkylcyclohexanecarboxylic acid-4-alkylphenyl esters, trans-4-alkylcyclohexanecarboxylic acid-4-alkoxyphenyl esters, 4-alkoxybenzoic acid-4-alkylphenyl esters, 4-alkylbenzoic acid-4-cyanophenyl esters, 4-(trans-4-alkylcyclohexyl)benzoic acid-4-cyanophenyl esters, etc., Schiff's base liquid crystal compounds such as 4-alkoxybenzylidene-4-alkanoyloxyanilines, 4-alkoxybenzylidene-4-alkylanilines, 4-alkoxybenzylidene-4-cyanoanilines, etc., biphenyl liquid crystal compounds such as 4'-alkyl-4-cyanobiphenyls, 4'-alkoxy-4-cyanobiphenyls, 4'-alkoxy-4-alkylbiphenyls, etc., phenylcyclohexane compounds such as trans-4-alkyl(4-cyanophenyl)cyclohexanes, trans-4-alkyl-(4-alkoxyphenyl)cyclohexanes, etc., heterocyclic liquid crystal compounds such as 5-alkyl-2-(4-cyanophenyl)-1,3-dioxanes, 5-alkyl-2-(4-cyanophenyl)-pyrimidines, 5-cyano-2-(4-alkylphenyl)pyrimidines, etc.

The content of the compounds of the present invention in the compositions of the present invention varies depending on the kind of other components to be mixed with the compounds, but usually it is in the range of 1 to 30% by weight, preferably 5 to 15% by weight. A concrete example is as follows: 1 to 30% by weight of the phenylpyridines of the present invention mixed with 70 to 99% by weight of one kind or a mixture of several kinds of trans-4-alkyl-(4-cyanophenyl)cyclohexanes, preferably 5 to 15% by weight of the former mixed with 85 to 95% by weight of the latter.

Another example is as follows:
a composition consisting of 60 to 84% by weight of one kind or a mixture of several kinds of trans-4-alkyl-(4-cyanophenyl)cyclohexanes, 10 to 15% by weight of one kind or a mixture of several kinds of 4-(trans4-alkyl-cyclohexyl)-4'-cyanobiphenyls and 1 to 30% by weight of the phenylpyridines of the present invention. A more desirable composition is as follows: 72 to 81% by weight, 12 to 15% by weight and 5 to 15% by weight in the order of the above compounds.

The present invention will be described in more detail by way of Examples, but it should not be construed to be limited thereto.

EXAMPLE 1

5-(Trans-4-propylcyclohexyl)-2-(4-fluorophenyl)pyridine

An ether solution (100 cc) of 4-fluorophenyl β-chlorovinyl ketone (11.4 g) was dropwise added with stirring to an ether solution (50 cc) of trans-4-propylβ-piperidinovinyl)cyclohexane (14.5 g) and triethylamine (6.3 g), followed by agitating the mixture at room temperature for 15 hours, adding water to the reaction mixture, separating the resulting ether layer, twice washing it with water, distilling off the solvent, mixing the residue, 70% perchloric acid aqueous solution (30 cc) and water (20 cc), refluxing the mixture for 30 minutes, cooling the resulting material, filtering off deposited precipitates, twice washing with water, mixing with a solution of acetic acid (120 cc) and ammonium acetate (40 g), refluxing the mixture for 5 hours, pouring it in ice water (300cc), extracting the resulting product with toluene (200 cc), washing the toluene layer with water, distilling off the solvent and a low boiling fraction, dissolving the residue in toluene, passing the solution through an alumina column, distilling off the solvent and recrystallizing the resulting raw product from ethanol to obtain the objective 5-(trans-4-propylcyclohexyl)-2-(4-fluorophenyl)pyridine (3.5 g). This product had the following phase transition points:
crystalline-nematic point: 99.0° C.
smectic-nematic point: (76.5° C.)
nematic-clearing point: 157.3° C.
The description inside the above parenthesis indicates a monotropic phase transition.

In the same manner as above, compounds described in the following Examples 2–4 were obtained from the corresponding trans-4-alkyl-(β-piperidinovinyl)cyclohexanes and -substituted-phenyl β-chlorovinyl ketones:

EXAMPLE 2

5-(Trans-4-propylcyclohexyl)-2-(3,4-difluorophenyl)-pyridine

Crystalline-nematic point: 59.1° C., nematic-clearing point: 109.1° C.

EXAMPLE 3

5-(Trans-4-butylcyclohexyl)-2-(4-ethylphenyl)pyridine

Crystalline-smectic point: 35.4° C., smectic-nematic point: 171.1° C., nematic-clearing point: 173.2° C.

EXAMPLE 4

5-(Trans-4-hexylcyclohexyl)-2-[4-(trans-4-propylcyclohexyl)phenyl]pyridine

Crystalline-smectic point: 90.0° C., smectic-nematic point: 266.5° C., nematic-clearing point: 300° C. or higher.

EXAMPLE 5

5-(Trans-4-hexylcyclohexyl)-2-(4-cyanophenyl)pyridine

Example 1 was repeated except that 4-fluorophenyl β-chlorovinyl ketone in Example 1 was replaced by 4-bromophenyl β-chlorovinyl ketone and also trans-4-propyl(β-pyridinovinyl)cyclohexane therein was replaced by trans-4-hexyl-(β-piperidinovinyl)cyclohexane, to obtain 5-(trans-4-hexylcyclohexyl)-2-(4-bromophenyl)pyridine.

A mixture of this product (10.3 g), cuprous cyanide (7.0 g) and N-methylpyrrolidone (50 cc) was refluxed for 3 hours, followed by cooling the resulting material, pouring it in a mixture of 25% aqueous ammonia (40 cc) and water (100 cc), extracting the resulting material with toluene (150 cc), washing the toluene layer with water, distilling off the solvent and a low boiling fraction, dissolving the residue in toluene, passing the solution through an alumina column, distilling off the solvent and recrystallizing the residue from ethanol to obtain the objective 5-(trans-4-hexylcyclohexyl)-2-(4-cyanophenyl)pyridine (5.0 g). This product had a crystalline-nematic point of 114.2° C. and a nematicclearing point of 217.7° C.

EXAMPLE 6

(Application example)

A liquid crystal composition (A) consisting of

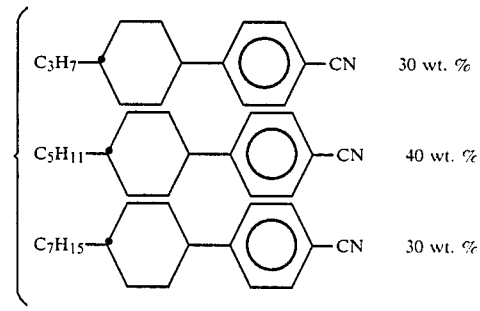

has a nematic-clearing point of 52.1° C., a viscosity at 20° C. of 23.4 cP, a dielectric anisotropy value (hereinafter abbreviated to Δε) of +11.2 and an optical anisotropy value (hereinafter abbreviated to Δn) of 0.119.

When this liquid crystal composition (A) was sealed in a TN cell of 10 μm thick, the resulting liquid crystal cell had a threshold voltage at 20° C of 1.54 V and a saturation voltage of 2.13 V. A composition (B) consisting of 85% by weight of this liquid crystal composition (A) and 15% by weight of 5-(trans-4-propylcyclohexyl)-2-(3,4-difluorophenyl)pyridine prepared in Example 2 had a nematic-clearing point of 56.0° C., a viscosity at 20° C. of 24.3 cP, a Δε of + 12.0 and a Δn of 0.124. When this composition was sealed in the same cell as above, the resulting liquid crystal cell had a threshold voltage of 1.47 V and a saturation voltage of 2.04 at 20° C.

EXAMPLE 7

(Application example)

When 15% by weight of 5-(trans-4-propylcyclohexyl)2-(4-fluorophenyl)pyridine prepared in Example 1 was added to 85% by weight of the liquid crystal composition (A) described in Example 6, the resulting nematic liquid crystal composition had a nematic-clearing point of 61.5° C., a viscosity at 20° C. of 22.8 cP, a Δε of +11.9 and a Δn of 0.127.

We claim:

1. A fluorophenylpyridine compound of the formula:

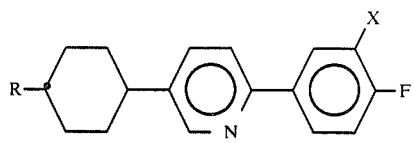

wherein R represents an alkyl group of 1 to 10 carbon atoms and X represents a fluorine or hydrogen atom.

2. A 5-(trans-4-alkylcyclohexyl)-2-(4-fluorophenyl)-pyridine compound according to claim 1, wherein X represents a hydrogen atom.

3. A 5-(trans-4-alkylcyclohexyl)-2-(3,4-difluorophenyl)pyridine compound according to claim 1.

4. A liquid cryustal composition containing at least two components, at least one of which is a fluorophenylpyridine compound according to claim 1.

* * * * *